US008669071B2

(12) United States Patent
Devulder et al.

(10) Patent No.: US 8,669,071 B2
(45) Date of Patent: Mar. 11, 2014

(54) METHOD FOR ESTIMATING THE NUMBER OF MICROORGANISMS IN A SAMPLE AND DEVICE FOR IMPLEMENTING SAID METHOD

(75) Inventors: Grégory Devulder, Thurins (FR); Catherine Arthaud, Villeurbanne (FR); Pierre-Jean Cotte-Pattat, Lagnieu (FR); Jean-Claude Raymond, Bessenay (FR)

(73) Assignee: Biomerieux, Marcy l'Etoile (FR)

( * ) Notice: Subject to any disclaimer, the term of this patent is extended or adjusted under 35 U.S.C. 154(b) by 0 days.

(21) Appl. No.: 13/635,126

(22) PCT Filed: Mar. 17, 2011

(86) PCT No.: PCT/FR2011/050543
§ 371 (c)(1),
(2), (4) Date: Sep. 14, 2012

(87) PCT Pub. No.: WO2011/014062
PCT Pub. Date: Sep. 22, 2011

(65) Prior Publication Data
US 2013/0004989 A1    Jan. 3, 2013

(30) Foreign Application Priority Data
Mar. 19, 2010 (FR) ...................................... 10 52010

(51) Int. Cl.
*C12Q 1/06*   (2006.01)
*C12N 1/00*   (2006.01)
*G11C 17/00*  (2006.01)
*G05B 15/00*  (2006.01)

(52) U.S. Cl.
USPC .................... 435/39; 435/243; 365/94; 700/1

(58) Field of Classification Search
USPC .................................................. 435/243, 39
See application file for complete search history.

(56) References Cited

U.S. PATENT DOCUMENTS 6,458,553 B1   10/2002 Colin et al.
2008/0113404 A1   5/2008 Eden et al.

FOREIGN PATENT DOCUMENTS

FR    2782729 A1    3/2000

OTHER PUBLICATIONS

International Search Report for PCT/FR2011/050543, mailed Jun. 30, 2011.
Juneja et al., Mathematical modeling of growth of Salmonella in raw ground beef under isothermal conditions from 10 to 45 degrees C. Int J Food Microbiol. May 31, 2009;131(2-3):106-11. Epub Feb. 5, 2009.
Lu et al., Application of predictive models to estimate Listeria monocytogenes growth on frankfurters treated with organic acid salts. J Food Prot. Nov. 2005;68(11):2326-32.

*Primary Examiner* — John S Brusca
*Assistant Examiner* — Srikanth Patury
(74) *Attorney, Agent, or Firm* — Norton Rose Fulbright Canada LLP

(57) ABSTRACT

A method for counting microorganisms present in a biological sample in contact with a culture medium adapted to the growth of said microorganisms,
Number $N_{SA}$ of microorganisms present in the sample is determined at a prior stage,
Number $N_{SU}$ of microorganisms present at a subsequent stage is calculated according to number $N_{SA}$. The calculation is based on a model of microorganism growth in the culture medium according to:

$$\log(N_{SU}) = \alpha \times \log(N_{SA}) - \beta \times \log(C_{SA}) + \gamma,$$

where log is the decimal logarithm, $N_{SU}$ is the calculated number of microorganisms, $N_{SA}$ is the number of microorganisms at the prior stage, $C_{SA}$ is the number of microorganisms at the prior stage divided by the volume of the sample, and $\alpha$, $\beta$, and $\gamma$ are determined parameters depending on the microorganisms, the culture medium, and the time period separating the subsequent stage from the prior stage, $\alpha$ and $\beta$ being positive.

11 Claims, 1 Drawing Sheet

METHOD FOR ESTIMATING THE NUMBER OF MICROORGANISMS IN A SAMPLE AND DEVICE FOR IMPLEMENTING SAID METHOD

RELATED APPLICATIONS

The present application is a national stage filing under 35 U.S.C. §371 of international PCT application, PCT/FR2011/050543, filed Mar. 17, 2011, which claims priority to French patent application, FR 1052010, filed Mar. 19, 2010, each of which is incorporated herein by reference.

BACKGROUND

The invention relates to the counting of microorganisms, such as bacteria and/or fungi, present in a biological sample.

DISCUSSION OF THE RELATED ART

The counting of microorganisms present in a biological sample is particularly important in a number of fields, and more specifically in food safety.

The marketing of a food product is submitted, for obvious safety reasons, to strict rules relative to the maximum acceptable bacterial load to be contained by the product. Quality controls are thus implemented to make sure that the concerned food product is fit for consumption and can thus be sold.

Usual quality controls essentially comprise a first step of preparation of a biological sample based on the product to be tested, followed by a second test of counting of the microorganisms present in this sample after incubation. As soon as the counted number of microorganisms exceeds a predetermined threshold, it is then considered that the tested product is unfit for consumption and it is thus not put for sale, or is removed from the market if it had already been put for sale.

However, whatever the used counting method, the sample has to be submitted to an incubation of variable duration according to the tested product and to the used culture medium. Indeed, according to the implemented method, the incubation time necessary to obtain a counting of microorganisms may vary from 24 h to 5 days. In the case of the counting of total flora of a sample, the incubation time is at least 48 h at 35° C., or even 72 h at 30° C. Thus, for a raw food product, only the counting after a minimum 40 hours of incubation, and more specifically at least 48 hours in the case of raw meat, is considered as reliable.

However, some forty hours is an excessively long time as compared with the lifetime of certain products. Indeed, for example, the lifetime of raw meat does not exceed a few days. While the marketing process is already engaged for a product to be put for sale as soon as quality tests are positive, a finally negative result forbids this putting for sale, which causes a significant economic loss.

The usefulness of a counting method which greatly decreases the incubation time while providing a counting substantially as reliable as that obtained after a long incubation time can thus easily be imagined.

SUMMARY

The invention aims at providing a method and a device which provide such a result.

For this purpose, the invention aims at a method for counting microorganisms present in a biological sample in contact with a culture medium adapted to the growth of said microorganisms.

According to the invention, the method comprises the steps of:
 determining at a prior stage number $N_{SA}$ of microorganisms present in the sample
 calculating number $N_{SU}$ of microorganisms present at a subsequent stage according to number $N_{SA}$, the calculation being based on a model of growth of microorganisms in the culture medium according to the following relation:

$$\log(N_{SU}) = \alpha \times \log(N_{SA}) - \beta \times \log(C_{SA}) + \gamma$$

where log is the decimal logarithm, $N_{SU}$ is the calculated number of microorganisms, $N_{SA}$ is the number of microorganisms at the prior stage, $C_{SA}$ is the number of microorganisms at the prior stage divided by the volume of the sample, and $\alpha$, $\beta$, and $\gamma$ are determined parameters depending on the microorganisms, on the culture medium, and on the time period separating the subsequent stage from the prior stage, $\alpha$ and $\beta$ being positive.

According to the invention, phrase "number of microorganisms" should be understood in the widest sense. It can thus be the real number of microorganisms or the number of colonies of microorganisms (for example, in Colony-forming Units).

"Based on a model" here refers to any calculation using said model, be it directly in the above-discussed mathematical form or under an equivalent mathematical form.

In other words, due to the model used, the number of microorganisms, bacteria and/or fungi present in the biological sample after a normally necessary incubation time period is reliably extrapolated from a number of microorganisms counted after a shorter real incubation period. A time gain equal to the difference between the normally necessary and real incubation times.

According to an embodiment of the invention, the method comprises determining the number of microorganisms at the prior stage, said estimate at the prior stage comprising:
 dividing the sample into several identical assemblies of identical volume or of at least two different volumes, according to a predetermined proportionality factor;
 applying culture conditions to said volumes, and especially an incubation at a predetermined temperature for a predetermined time period, to have the number of microorganisms increase in the volumes;
 detecting the presence or the absence of microorganisms in the volumes after having applied the culture conditions; and
 calculating the number of microorganisms in the sample by the most probable number (MPN) method.

According to an embodiment of the invention, the method comprises a step of preparation of the biological sample from a food product portion.

According to a specific embodiment where the total flora is counted in a fresh product with an adequate culture medium by means of instrument TEMPO® sold by the applicant, the prior stage corresponds to approximately 24 hours after the preparation of the sample and the subsequent stage corresponds to approximately 48 hours after the preparation of the sample.

The invention also aims at a device for counting microorganisms present in a biological sample in contact with a culture medium adapted to the growth of said microorganisms, comprising means forming a sample receiver, and means for measuring or estimating the number of microorganisms present in a sample arranged in the sample receiver.

According to the invention, the device further comprises means for calculating the number of microorganisms present in the sample according to the number of microorganisms measured or estimated by the measurement or estimating means, based on a model of growth of the microorganisms according to the following relation:

$$\log(N_{SU}) = \alpha \times \log(N_{SA}) - \beta \times \log(C_{SA}) + \gamma$$

where log is the decimal logarithm, $N_{SU}$ is the number of microorganisms calculated at the subsequent stage, $N_{SA}$ is the number of microorganisms determined at the prior stage, $C_{SA}$ is the number of microorganisms at the prior stage divided by the sample volume, and $\alpha$, $\beta$, and $\gamma$ are determined parameters depending on the sample, on the culture medium, and on the time period separating the subsequent stage from the prior stage, $\alpha$ and $\beta$ being positive.

The invention also aims at a computer program product comprising instructions, stored on a computer-readable recording support, to implement the method of the previously-mentioned type when the program is executed by a computer.

BRIEF DESCRIPTION OF THE DRAWINGS

The invention will be better understood from the following non-limiting description, in connection with the accompanying drawings, among which.

DETAILED DESCRIPTION

Figure 1:
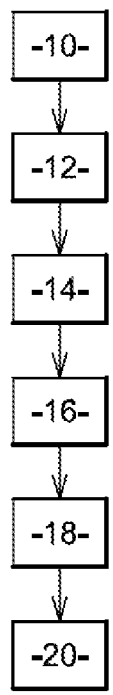
FIG. 1 is a flowchart of a method according to the invention.

Referring to FIG. 1, a method according to the invention comprises a first step 10 of preparation of a biological sample from a product to be tested.

For example, to count the microorganisms present in raw meat, essentially bacteria, a predetermined mass of this meat is placed in a Stomacher bag with a volume of peptone water. The mixture is homogenized in the bag for several minutes. The obtained liquid is then submitted to an additional dilution by transfer of a volume contained in the Stomacher bag into a vial containing a volume of culture medium. A liquid biological sample is then obtained, this sample being submitted to the counting according to the invention.

Conventionally, the culture medium is selected according to the type of microorganisms which are searched for in the biological sample, and the number of which is desired to be known after a given incubation time period. The culture medium has a wide spectrum, that is, adapted to the growth of a large number of microorganisms of different types capable of being present in the tested product, or is selected to be suitable for the growth of a limited number of microorganism types, or even for a single microorganism type. The selection of the culture medium depends on the targeted application, as known per se in that art. For example, in the case of raw meat, a wide-spectrum culture medium is preferred.

Once the biological sample has been obtained, it is then prepared, at step 12, to be submitted to a counting of colony-forming units per gram (CFU/g) by using the most probable number method (or MPN method).

More specifically, the sample is distributed between several identical sets of N isolated transparent cavities, of proportional volume, formed in an analysis card. Conventionally, each assembly has three cavities, the volume of the large cavity being 10 times greater than the volume of the medium cavity, which itself has a volume 10 times greater than the volume of the small cavity. Preferably, the biological sample is distributed by means of an analysis card such as described in document EP 1105457, which has the advantage of reliably automating the sample distribution between several transparent cavities, while isolating them from one another.

The analysis card is then submitted for a predetermined time period, at step 14, to conditions promoting the growth of the microorganisms which are desired to be counted, especially an incubation at a given temperature, for example, between 30° C. and 35° C. for microorganisms contained in food products.

Once the incubation time is over, the method continues, at step 16, with the optical detection of the presence or the absence of microorganisms in each of the cavities of the analysis card. According to the selected culture medium, it is indeed possible to grow certain microorganisms. Now, the microorganism growth modifies the optical density or the coloring of the content of a cavity (for example, in the case where fluorescent or chromogenic markers are used in the culture medium), as known per se in the art. A measurable modification of the optical properties of a cavity thus means a microbial development inside of it, the opposite meaning no microbial development.

Preferably, in the case of the analysis of a fresh product, an incubation lasting between 20 and 40 hours provides a reliable estimate of the number of microorganisms between 40 and 76 hours, with regard to the implemented optical detection and to the MPN method. In particular, in the case of a raw meat analysis by means of detection system TEMPO® TVC sold by bioMérieux, an estimate of the number of microorganism between 40 and 48 hours may be obtained between 20 and 36 hours.

Once the presence or the absence of a microorganism development has been determined in each of the cavities of the analysis card, a counting of the number of colony-forming units per gram is performed, at step 18, by using the MPN method, and preferentially J. C. De Man's method. Reference will for example be made to document EP 1105457 for more details relative to this method.

A number of colony-forming units per gram of tested product, and thus the number of colony-forming units present in the biological sample, are thus obtained. This last number differs from the first number by a proportionality factor taking into account the various dilutions used to prepare the sample and of the volumes of the previously-sampled sample.

The method then carries on, at step 20, by estimating by calculation the number of colony-forming units which would be obtained by a normally necessary longer incubation of the biological sample, for example, 48 hours for raw meats, according to the number of colony-forming units present in the sample counted after the real incubation, according to the following relation:

$$\log(N_{SU}) = \alpha \times \log(N_{SA}) - \beta \times \log(C_{SA}) + \gamma$$

where log is the decimal logarithm, $N_{SU}$ is the number estimated for the normally-necessary incubation, $N_{SA}$ is the number of colony-forming units in the sample counted after the real incubation, $C_{SA}$ is this same number divided by the volume of the biological sample, and $\alpha$, $\beta$ and $\gamma$ are predetermined positive parameters depending on the microorganisms, on the culture medium, and on the time period separating the normally necessary incubation from the real incubation.

It should here be noted that this calculation may be performed even while the incubation carries on, the analysis card being for example arranged in an incubation chamber provided with optical detection means connected to a data processing unit implementing the MPN method and the counting according to the present invention.

Parameters α, β and γ are determined offhand according to the following procedure:
a) preparing a statistically significant number of biological samples from a type of product to be tested at a subsequent stage (for example, raw meat) at different contamination stages;
b) incubating said samples during the incubation time which will be used for the counting on which the estimate is based, and counting the number of microorganisms in said samples after incubation;
c) continuing the incubation of the samples all the way to the subsequent stage desired for the estimate, and counting the number of microorganisms in the samples after this additional incubation; and
d) identifying by a statistical method the parameters of the model, for example, by means of an adjustment in the logarithmic space.

The method is preferentially implemented by means of diagnosis system TEMPO®, this diagnosis system using the analysis cards described in document EP 1105457.

System TEMPO® comprises a data processing unit, for example, a microcontroller, connected to the optical detection circuit to implement the counting according to the MPN method based on the detection results. According to the present invention, this device is modified so that the data processing unit is further capable of implementing the estimate according to the invention.

Advantageously, the data processing unit stores different sets of parameters α, β and γ, and the user can select, by means of an interface connected to the data processing unit, the appropriate assembly for the biological sample in the analysis card and the incubation time for which the estimate is performed.

An example of microorganism counting in raw meat implemented by means of system TEMPO® is described hereinafter.

A biological sample is first prepared. A tenfold primary dilution is prepared by mixing 10 g of the sample with a volume of 90 milliliters (ml) of primary diluents, such as peptone water in a Stomacher bag. The mixture is homogenized in the bag for from 1 to 2 minutes.

Then, TEMPO® cards are prepared with the culture medium.

The TEMPO® TVC culture medium is reconstituted by distributing 3 ml of secondary diluent, for example, in a TEMPO® TVC vial.

By means of a sterile pipette, 1 ml is then sampled from the filtered compartment of the Stomacher bag and is transferred into the TEMPO® TVC vial containing the reconstituted culture medium, to inoculate said medium. The mixture is homogenized by means of a vortex-type agitator for approximately 3 seconds. The obtained 4 ml of inoculated medium thus correspond to a 1/40 dilution of the sample.

The vial containing the inoculated medium is placed on a filling rack. The corresponding TEMPO® card is placed on the rack in front of the vial, the transfer tube of the card being dipped into the vial.

The rack containing the vials and the cards, in fluid connection, is placed in the TEMPO® Filler. The filling cycle is thus started. The inoculated medium is totally sucked into the card. After being filled, the cards are isolated from the outer environment by cutting and sealing of the transfer tubes.

The filling rack is taken out of the TEMPO® Filler. The cards are removed from the rack and transferred onto incubation racks.

The cards are then incubated at a 35° C. temperature for the counting of the total flora.

The method then continues with the reading of the cards.

After 24 h of incubation, the reading racks are placed in the TEMPO® Reader. The preliminary reading is then automatically performed. For each of the card wells, the system defines the positiveness, then transforms it into a MPN combination.

Based on the obtained combination and on the applied dilution factor, the system automatically calculates the microorganism concentration in the sample. The defined mathematical model is then applied to obtain the final estimated result.

The number of microorganisms which would be present in the samples after 48 hours of incubation at 35° C. has been estimated from a counting performed after 24 hours of incubation at 35° C., by means of the following model:

$$\log(N_{SU}) = 1.072 \times \log(N_{SA}) - 0.232 \times \log(C_{SA}) + 0.94$$

Figure 2:
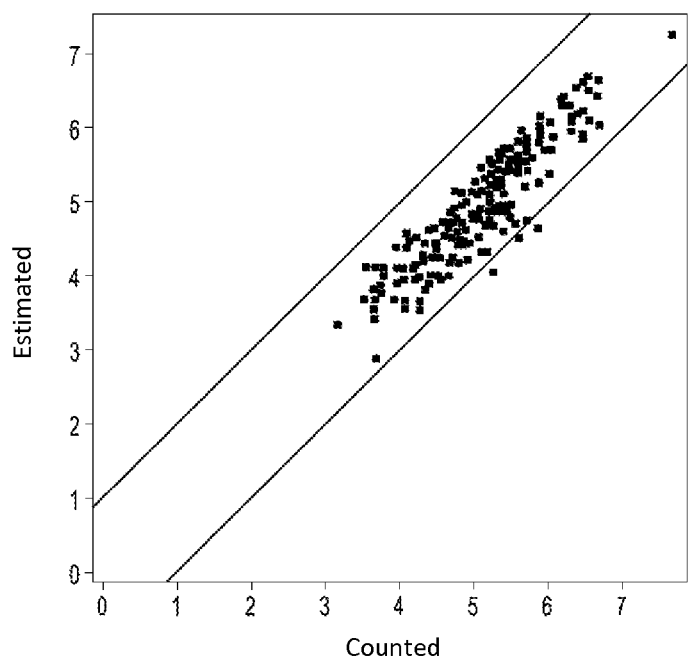
FIG. 2 is an experience plot with, as abscissas, counts of colonies performed after 48 hours of incubation of different biological samples originating from raw meats and, as ordinates, the estimated counting according to the invention.

The experimental results are shown in the plot of FIG. 2. The abscissas of this drawing show the counted number of microorganisms in the samples after a real 48-hours incubation at 35° C. The ordinates show the corresponding estimated numbers of microorganisms in the samples based on the numbers of microorganisms counted after a real 24-hour incubation.

As can be seen, a very strong correlation between the real measurement of the number of microorganisms at 48 hours and the estimate of this same number can be observed, both numbers differing by less than 0.5 log.

It is thus possible to obtain a reliable result after 24 hours of what the number of microorganisms would be at 48 hours. Thus, 24 hours in advance, it is possible to take the adequate measures in the case where the number estimated at 48 hours would not comply with food safety requirements.

Although the MPN method has been described to perform the counting, other methods may be used. The MPN method however has the advantage of being automatable, whereby only the preparation of the biological sample would then be performed manually. Of course, the number of microorganisms according to the present invention may also be estimated according to a manual counting of colonies present on a Petri dish after a given incubation time.

Although an application to the counting of microorganisms in a food product, and especially raw meat, has been described, other products such as, for example, vegetables, fish, or any other product with a short lifetime may be tested.

The invention claimed is:

1. A method for counting microorganisms present in a biological sample in contact with a culture medium adapted to the growth of said microorganisms, wherein the method comprises executing on a data processing unit program code for:
determining at a prior stage number $N_{SA}$ of microorganisms present in the sample;
calculating number $N_{SU}$ of microorganisms present in the sample according to number $N_{SA}$, the calculation being based on a model of microorganism growth in the culture medium according to the following relation:

$$\log(N_{SU}) = \alpha \times \log(N_{SA}) - \beta \times \log(C_{SA}) + \gamma$$

where log is the decimal logarithm, $N_{SU}$ is the calculated number of microorganisms, $N_{SA}$ is the number of microorganisms at the prior stage, $C_{SA}$ is the number of microorganisms at the prior stage divided by the volume of the sample, and α, β, and γ are determined parameters depending on the microorganisms, on the culture medium, and on the time period separating a subsequent stage from the prior stage, α and β being positive.

2. The method of claim 1, wherein the method comprises executing on a data processor program code for determining the number of microorganisms at the prior stage, said determining at the prior stage comprising:
dividing the sample into several identical assemblies of identical volume or of at least two different volumes, according to a predetermined proportionality factor;
applying culture conditions to said volumes, and especially an incubation at a predetermined temperature for a predetermined time period, to have the number of microorganisms grow in these volumes;
the presence or the absence of microorganisms in the volumes after having applied the culture conditions; and
calculating the number of microorganisms in the sample by the most probable number method.

3. The method of claim 1, wherein the method comprises a step of preparation of the biological sample from a portion of food product.

4. The method of claim 1, wherein the prior stage corresponds to approximately 24 hours after preparation of the sample and in that the subsequent stage corresponds to approximately 48 hours after the preparation of the sample.

5. A device for counting microorganisms present in a biological sample in contact with a culture medium adapted to the growth of said microorganisms, comprising an analysis card adapted to receive therein a sample and a data processor for measuring or estimating the number of microorganisms present in the sample arranged in the analysis card, the data processor configured for calculating the number of microorganisms present in the sample according to the number of microorganisms at a prior stage measured or estimated by the data processor, based on a model of growth of the microorganisms according to the following relation:

$$\log(N_{SU}) = \alpha \times \log(N_{SA}) - \beta \times \log(C_{SA}) + \gamma$$

where log is the decimal logarithm, $N_{SU}$ is the calculated number of microorganisms, $N_{SA}$ is the measured or estimated number of microorganisms at the prior stage, $C_{SA}$ is the number of microorganisms at the prior stage divided by the volume of the sample, and α, β, and γ are determined parameters depending on the microorganisms, on the culture medium, and on the time period separating a subsequent stage from the prior stage, α and β being positive.

6. A computer program product comprising instructions, stored on a non-transitory computer-readable recording support, for implementing the method of claim 1 when the program is executed by a computer.

7. The method of claim 2, wherein the method comprises a step of preparation of the biological sample from a portion of food product.

8. The method of claim 2, wherein the prior stage corresponds to approximately 24 hours after preparation of the sample and in that the subsequent stage corresponds to approximately 48 hours after the preparation of the sample.

9. The method of claim 3, wherein the prior stage corresponds to approximately 24 hours after the preparation of the sample and in that the subsequent stage corresponds to approximately 48 hours after the preparation of the sample.

10. The method of claim 7, wherein the prior stage corresponds to approximately 24 hours after the preparation of the sample and in that the subsequent stage corresponds to approximately 48 hours after the preparation of the sample.

11. The method of claim 1, further comprising executing on a data processor program code for comparing the calculated number $N_{SU}$ of microorganisms present in the sample to a predetermined threshold and determining that a product the sample is based on is unfit for consumption if the calculated number $N_{SU}$ of microorganisms exceeds the predetermined threshold.

* * * * *